(12) United States Patent
Zhang et al.

(10) Patent No.: US 11,079,313 B2
(45) Date of Patent: Aug. 3, 2021

(54) METHODS AND SYSTEMS FOR DETERMINING CORE PERMEABILITY PULSE DECAY EXPERIMENTS

(71) Applicant: Saudi Arabian Oil Company, Dhahran (SA)

(72) Inventors: Jilin Jay Zhang, Cypress, TX (US); Hui-Hai Liu, Katy, TX (US); Huangye Chen, Cypress, TX (US)

(73) Assignee: Saudi Arabian Oil Company, Dhahran (SA)

( * ) Notice: Subject to any disclaimer, the term of this patent is extended or adjusted under 35 U.S.C. 154(b) by 203 days.

(21) Appl. No.: 16/414,968

(22) Filed: May 17, 2019

(65) Prior Publication Data
US 2020/0363310 A1    Nov. 19, 2020

(51) Int. Cl.
*G01N 15/08* (2006.01)
*G01N 33/24* (2006.01)
*E21B 49/08* (2006.01)

(52) U.S. Cl.
CPC ....... *G01N 15/0826* (2013.01); *E21B 49/088* (2013.01); *G01N 15/0806* (2013.01); *G01N 15/088* (2013.01)

(58) Field of Classification Search
CPC .... G01N 15/00; G01N 15/08; G01N 15/0806; G01N 15/082; G01N 15/088; G01N 33/24; G01N 2015/0846; E21B 49/00; E21B 49/088
See application file for complete search history.

(56) References Cited

U.S. PATENT DOCUMENTS

| | | | | |
|---|---|---|---|---|
| 9,335,245 | B2 * | 5/2016 | Song | G01N 15/08 |
| 9,989,512 | B2 | 6/2018 | Haggerty | |
| 10,302,543 | B2 * | 5/2019 | Hannon, Jr. | G01N 1/28 |
| 10,613,014 | B2 * | 4/2020 | Hender | G01N 15/0826 |
| 10,677,707 | B2 * | 6/2020 | Dusterhoft | E21B 49/00 |

(Continued)

FOREIGN PATENT DOCUMENTS

WO    2017015035 A1    1/2017

OTHER PUBLICATIONS

Alnoaimi, K.R.; "Experimental and Numerical Analysis of Gas Transport in Shale Including the Role of Sorption" SPE166375, SPE Annual Technical Conference and Exhibition, New Orleans Sep. 30-Oct. 2, 2013; pp. 1-16.

(Continued)

*Primary Examiner* — Nguyen Q. Ha
(74) *Attorney, Agent, or Firm* — Bracewell LLP; Constance G. Rhebergen; Vivek P. Shankam (57) ABSTRACT

Methods and systems method for determining core permeability of a subsurface formation. The method includes connecting an upstream reservoir to one end of a sample holder comprising a core sample of a subsurface formation, connecting a downstream reservoir to another end of the sample holder, providing a constant confining pressure within the sample holder, saturating the sample holder and the core sample with nitrogen at a saturation pressure, applying a pressure pulse to one end of the sample holder, and determining core permeability using the porosity of the mobile continuum when the pressure in the upstream reservoir, the downstream reservoir, and the mobile continuum is in equilibrium.

16 Claims, 6 Drawing Sheets

(56) References Cited

U.S. PATENT DOCUMENTS

| | | | |
|---|---|---|---|
| 10,845,292 B2* | 11/2020 | Georgi | G01N 15/0806 |
| 2013/0054157 A1* | 2/2013 | Lasseux | G01N 15/0826 |
| | | | 702/47 |
| 2015/0293007 A1 | 10/2015 | Ramakrishnan et al. | |
| 2015/0293008 A1 | 10/2015 | Ramakrishnan et al. | |
| 2016/0334322 A1 | 11/2016 | Ramakrishnan et al. | |
| 2017/0016812 A1 | 1/2017 | Liu et al. | |
| 2017/0167964 A1 | 6/2017 | Liu et al. | |
| 2018/0340878 A1 | 11/2018 | Liu et al. | |
| 2018/0348111 A1 | 12/2018 | Hannon | |
| 2018/0364142 A1 | 12/2018 | Georgi et al. | |
| 2019/0353575 A1* | 11/2019 | Clarkson | G01N 15/0826 |

OTHER PUBLICATIONS

Dicker, A.I. et al.; "A Practical Approach for Determining Permeabiilty From Laboratory Pressure-Pulse Decay Measurements" SPE 17578, SPE International Meeting on Petroleum Engineering, Tianjin, China, Nov. 1-4, 1988; pp. 285-292.

Han, Guofeng et al.; "Analysis method of pulse decay tests for dual-porosity cores" Journal of Natural Gas Science and Engineering 59 (2018); pp. 274-286.

Jones, C et al.; "An experimental study of elastic wave propagation anisotropy and permeability anisotropy in an illitic shale" SPE/ISRM 47369, SPE/ISRM Eurock '98, Trondheim, Norway, Jul. 8-10, 1998; pp. 307-313.

Jones, S.C.; "A Technique for Faster Pulse-Decay Permeability Measurements in Tight Rocks" SPE 28450, SPE Formation Evaluation, Mar. 1997; pp. 19-25.

Liu, Hui-Hai et al.; "An Innovative Laboratory Method to Measure Pore-Pressure-Dependent Gas Permeability of Shale: Theory and Numerical Experiments" SPE 191123, 2018 SPE Reservoir Evaluation & Engineering; pp. 1-10.

Liu, Hui-Hai et al.; "Pressure pulse-decay tests in a dual-continuum medium: Late-time behavior" Journal of Petroleum Science and Engineering 147 (2016); pp. 292-301.

Luffel, D.L. et al; "Matrix Permeability Measurement of Gas Productive Shales" SPE 26633, 68th Annual Technical Conference & Exhibition of the Society of Petroleum Engineers, Houston, TX, Oct. 3-6, 1993; pp. 261-270.

Singh, H. et al.; "Nonempirical Apparent Permeability of Shale" SPE 170243, Aug. 2014 SPE Reservoir Evaluation & Engineering; pp. 414-424.

Singh, Harpreet; "Integration of Nonempirical Shale Permeability Model in a Dual-Continuum Reservoir Simulator" SPE 167125, SPE Unconventional Resources Conference—Canada, Nov. 5-7, 2013; pp. 1-11.

Cronin et al., "Dual-Permeability microstratigraphy in the Barnett Shale," Journal of Petroleum Science and Engineering, vol. 142, Feb. 3, 2016; pp. 119-128.

Cui et al., "Measurements of gas permeability and diffusivity of tight reservoir rocks: different approaches and their applications," Geofluids (2009) vol. 9, Aug. 4, 2009; pp. 208-223.

International Search Report and Written Opinion for International Application No. PCT/US2020/032994 report dated Aug. 26, 2020; pp. 1-17.

* cited by examiner

METHODS AND SYSTEMS FOR DETERMINING CORE PERMEABILITY PULSE DECAY EXPERIMENTS

TECHNICAL FIELD

Example embodiments relate to methods and systems for determining core permeability using the porosity of the mobile continuum.

BACKGROUND

Shale matrix permeability is an important parameter for characterizing a source rock reservoir and predicting hydrocarbon production from it. However, accurately measuring permeability of source rocks is a challenge for the oil and gas industry. Currently available methods for laboratory permeability measurement include steady state flow method on core plugs, transient pulse-decay on core plugs, and pressure decay on crushed rock samples. The preferred method is the pressure pulse-decay method given that the steady state measurement takes very long time and the pressure decay method generates results that are very sensitive to the particle size of crushed rock samples and the method itself is limited to the unconfined stress condition.

The pulse-decay test setup generally consists of two gas reservoirs and a sample holder with controlled confining stress for test samples. Then a pressure pulse is introduced from the upstream gas reservoir and pressure evolution in the upstream and downstream reservoirs are monitored. The permeability is estimated by fitting the corresponding analytical solution to pressure signals for a given core porosity and other parameters.

A commonly used pulse-decay method considers a core sample as a single continuum system and thus uses the total porosity in estimating permeability. Flow in a shale core is more accurately described by a dual-continuum system owing to its wide spread pore size distributions and property differences between organic and inorganic components of the shale matrix. A dual-continuum system includes a globally connected pore network, or mobile continuum, and an immobile continuum that consists of pores that are only locally connected to the globally connected pore network. The mobile continuum in the dual-continuum system contributes to core permeability while the immobile continuum generally contributes to the local storage. Some studies have theoretically shown that the analytical solutions for a single continuum can be used to estimate permeability for a dual-continuum system as long as the porosity for the mobile continuum, rather than the total porosity, is employed for permeability estimation.

SUMMARY

However, a practical technique for estimating the porosity for the mobile continuum and using it for permeability calculation in pulse decay experiments has not been developed yet. Example embodiments disclosed relate to improved methods and systems for estimating the porosity for the mobile continuum and using it for permeability calculation in pulse decay experiments.

Accordingly, one example embodiment is a method for determining core permeability of a subsurface formation by estimating the porosity for the mobile continuum and using it for permeability calculation in pulse decay experiments. The method includes connecting an upstream reservoir to one end of a sample holder comprising a core sample of a subsurface formation. The method further includes connecting a downstream reservoir connected to another end of the sample holder. The method further includes providing a constant confining pressure ($P_c$) within the sample holder. The method further includes saturating the sample holder and the core sample with nitrogen at a saturation pressure, $P_{saturation}$. The method further includes applying a pressure pulse, $P_{pulse}$, to one end of the sample holder, and determining core permeability using the porosity of mobile continuum when the pressure in the upstream reservoir, the downstream reservoir, and the mobile continuum is in equilibrium.

Another example embodiment is a system for determining core permeability of a subsurface formation by estimating the porosity for the mobile continuum and using it for permeability calculation in pulse decay experiments. The system includes a sample holder comprising a core sample of the subsurface formation, an upstream reservoir connected to one end of the sample holder, and a downstream reservoir connected to another end of the sample holder. The system also includes an inlet pump connected to the upstream reservoir, an outlet pump connected to the downstream reservoir, and a plurality of pressure sensors connected to the upstream reservoir, the downstream reservoir, and the sample holder. The system also includes a processor configured to receive signals from the plurality of pressure sensors, and determine the core permeability based on the pressure in the upstream reservoir and the pressure in the downstream reservoir.

Another example embodiment is a computer program stored in a computer readable medium for determining core permeability of a subsurface formation by estimating the porosity for the mobile continuum and using it for permeability calculation in pulse decay experiments. The non-transitory computer-readable media may have, for example, computer executable instructions that when executed by a processor, cause the processor to determine core permeability of the subsurface formation. This method may include connecting an upstream reservoir to one end of a sample holder comprising a core sample of a subsurface formation, connecting a downstream reservoir to another end of the sample holder, providing a constant confining pressure ($P_c$) within the sample holder, saturating the sample holder and the core sample with nitrogen at a saturation pressure, $P_{saturation}$, applying a pressure pulse, $P_{pulse}$, to one end of the sample holder, and determining core permeability of the subsurface formation using the general formula:

$$P_u(t) - P_d(t) = f(\Phi_f, L, A, V_{bulk}, c, \mu, V_f, V_u, V_d, k, t)$$

where '$\Phi_f$' is the porosity of the sample from the mobile continuum, 'L' is the sample length, 'A' is the cross-sectional area of the sample, '$V_{bulk}$' is the bulk volume of the sample (where $V_{bulk}$=L A; and $\Phi_f = V_f/V_{bulk}$), 'c' is the gas compressibility, '$\mu$' is the gas viscosity, '$V_f$' is the pore volume of the sample from the mobile continuum, '$V_u$' is the upstream reservoir volume, '$V_d$' is the downstream reservoir volume, '$P_u(t)$' is the pressure of the upstream side, '$P_d(t)$' is the pressure of the downstream side, 'k' is the sample permeability, and 't' is time. All units of the variables are in metric units.

DETAILED DESCRIPTION

The term "core" as used in this disclosure refers to a sample of a subsurface formation, such as a rock, obtained using a process commonly referred to as "coring" in the oil and gas industry. Such a rock sample or core sample generally has a major dimension and a minor dimension, where the major dimension is greater than the minor dimension, such as a cylinder.

Figure 1:
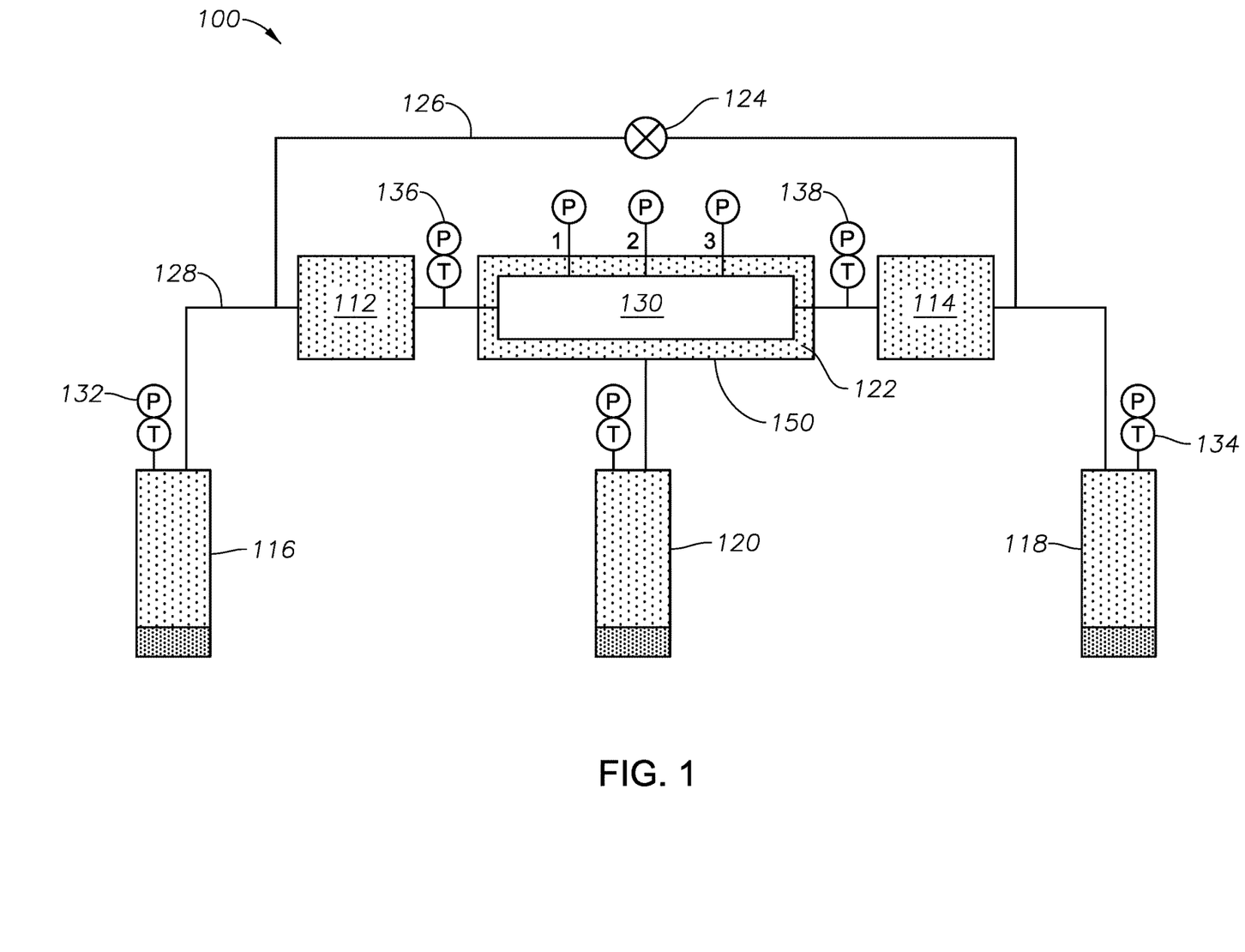
FIG. 1 illustrates system for determining core permeability of a subsurface formation, according to one example embodiment of the disclosure.

FIG. 1 illustrates a system 100 for determining core permeability of a subsurface formation, according to one example embodiment of the disclosure. System 100 includes sample 130, such as a shale sample, a limestone sample, or a sandstone sample, in the form of a cylinder or column that may be extracted from the subsurface for determining characteristics of the formation. The sample 130, after properly packaging, called sleeving, is placed in a sample holder 150 that may contain a confining fluid 122, such as gas, a water-based fluid, or an oil-based fluid. The sample holder 150 is coupled to pumps 116, 118 through pressure lines 128, and provides the confining pressure to the sample 130.

System 100 includes an inlet pump 116 configured to pump fluid from a first gas tank 112, for example, an upstream reservoir, into sample 130. The system also includes an outlet pump 118 configured to pump fluid from a second gas tank 114, for example, a downstream reservoir, into sample 130. Both pumps may include one or more pressure, temperature, and flowrate sensors 132 on the upstream side, and one or more pressure, temperature, and flowrate sensors 134 on the downstream side to measure and control the pressure inside the core sample assembly. Additional pressure and temperature sensors 136 and 138 may be installed for monitoring the gas pressure closer to the sample upstream and downstream end faces, respectively. Sample holder 150 may be equipped with a hydraulic pump 120, which may also be referred to as the confining pump, that may pump the confining fluid 122 into sample holder 150. The sample holder 150 may include an apparatus that monitors and regulates the pressure within the sample holder 150. Pressure, temperature, and flowrate gauges 132, 134 are coupled to the pressure lines 128 and the pumps 116, 118, 120. Both gauges may include transducers to measure temperature and pressure, respectively, in real-time, and may include an apparatus to measure and record the flowrate going out or coming into the pumps. The inlet to the core sample assembly may be diverted at one or more points using bypass valves 124 and an outlet pipe 126 in order to regulate the pore gas pressure (for example, the establishment of the initial pore pressure) in sample 130 which is placed in the sample holder 150.

One example embodiment is a method for determining porosity of a mobile continuum of a subsurface formation sample and using that porosity value in pulse-decay experiments to accurately determine core permeability. In one embodiment, the pulse-decay test setup may include two gas reservoirs and a sample holder with controlled confining stress for the test samples. A confining pressure ranging between 3,000 psi (pounds per square inch) and 10,000 psi is applied to the test sample in the sample holder. All of the components of the sample holder and the sample are saturated with nitrogen at a specified pressure, $P_{saturation}$ (for example, about 2,500 psi), for an extended time period so that all pores inside the test sample are filled with the nitrogen. Then, a pressure pulse $P_{pulse}$ (for example, about 100 psi) is applied on the upstream side and the pressure changes on both the upstream and downstream gas reservoirs is monitored and recorded.

The measured pressure signals, as a function of time, are fitted with an analytical solution. The pre-existing analytical solution can be written in a general form as:

$$P_u(t) - P_d(t) = f(\Phi_t, L, A, V_{bulk}, c, \mu, V_t, V_u, V_d, k, t) \quad (1)$$

where '$\Phi_t$' is the total porosity of the sample, 'L' is the sample length, 'A' is the cross-sectional area of the sample, '$V_{bulk}$' is the bulk volume of the sample (where $V_{bulk} = L*A$; and $\Phi_t = V_t/V_{bulk}$), 'c' is the gas compressibility, '$\mu$' is the gas viscosity, '$V_t$' is the total pore volume of the sample, '$V_u$' is the upstream reservoir volume, '$V_d$' is the downstream reservoir volume, '$P_u(t)$' is the pressure of the upstream side, '$P_d(t)$' is the pressure of the downstream side, 'k' is the sample permeability, and 't' is time. All variables are in metric units except the dimensionless ones. A few intermediary variables are given as follows:

$$t_D = \frac{kt}{c\mu\phi_t L^2}; \quad (2)$$

$$a = \frac{V_t}{V_u};$$

$$b = \frac{V_t}{V_d};$$

$$\tan\theta = \frac{(a+b)\theta}{(\theta^2 - ab)};$$

$$\Delta P(t_D) = \frac{P_u(t_D) - P_d(t_D)}{P_u(0) - P_d(0)} =$$

$$2 \sum_{m=1}^{\infty} \exp(-t_D \theta_m^2) \frac{a(b^2 + \theta_m^2) - (-1)^m b[(a^2 + \theta_m^2)(b^2 + \theta_m^2)]^{0.5}}{\theta_m^4 + \theta_m^2(a + a^2 + b + b^2) + ab(a + b + ab)}$$

where the $\theta$ equation has many solutions $\theta_m$ (m=1, 2, 3, ...).

The left-hand side of Equation (1) is measured pressure signals and the right-hand side represents a function of both time and related parameters. All these parameters are known except permeability 'k'. Thus Equation (1) can be solved for determining 'k'. The estimated 'k' value is determined by a set of given parameters, including the total porosity. However, flow in a source rock core is more accurately described by a dual-continuum system. The porosity for the mobile continuum, rather than the total porosity, should be employed for permeability estimation.

Figure 2:
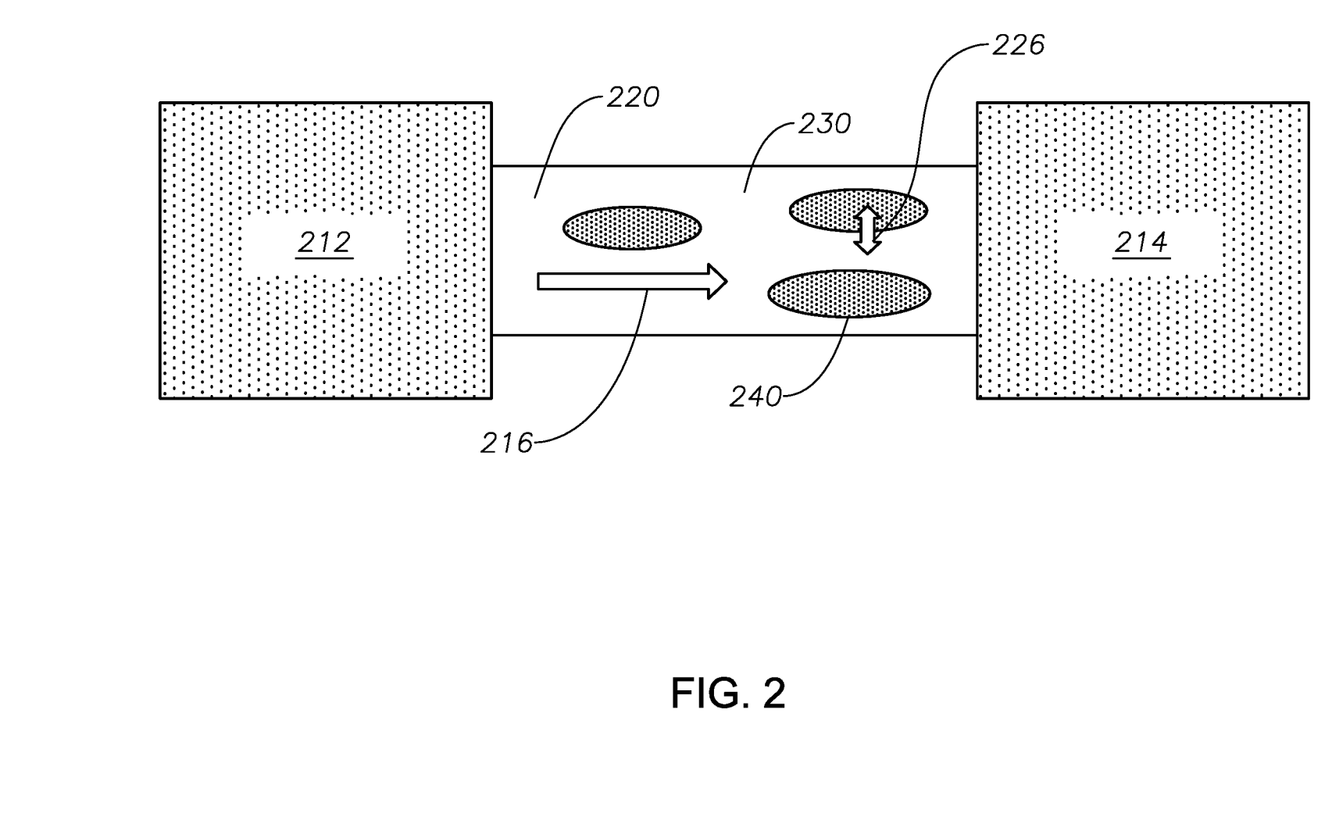
FIG. 2 illustrates a schematic diagram for a pulse-decay experiment using a core sample characterized by a dual-continuum, according to one example embodiment of the disclosure.

FIG. 2 shows a schematic diagram for a pulse-decay experiment for a core sample 230 characterized by a dual-continuum system. Initially, upstream gas reservoir 212, downstream gas reservoir 214, and pores in the core sample 230 are in equilibrium at a gas pressure of $P_{saturation}$. Then, the pressure in the upstream gas reservoir 212 is increased by $P_{pulse}$ (for example, 100 psi), which is generally a few percentages of $P_{saturation}$ (for example, 2,500 psi). After that, the upstream gas reservoir 212 is connected to the core sample 230 and gas flows through the core sample to the downstream gas reservoir along arrow 216. After gas flow occurs, the gas reservoirs are connected to core sample. Within the core sample, gas flows from the mobile continuum 220, which determines permeability, to the immobile continuum 240, which has a much lower permeability than the mobile continuum, along arrow 226 because of the pressure difference between the two continua.

Therefore, there is a need to differentiate the fraction of pores of the mobile continuum (that determines permeability) and the fraction of pores constituting the immobile continuum (that has much lower permeability than the mobile continuum) to better calculate the permeability in the pulse decay experiments.

Figure 3:
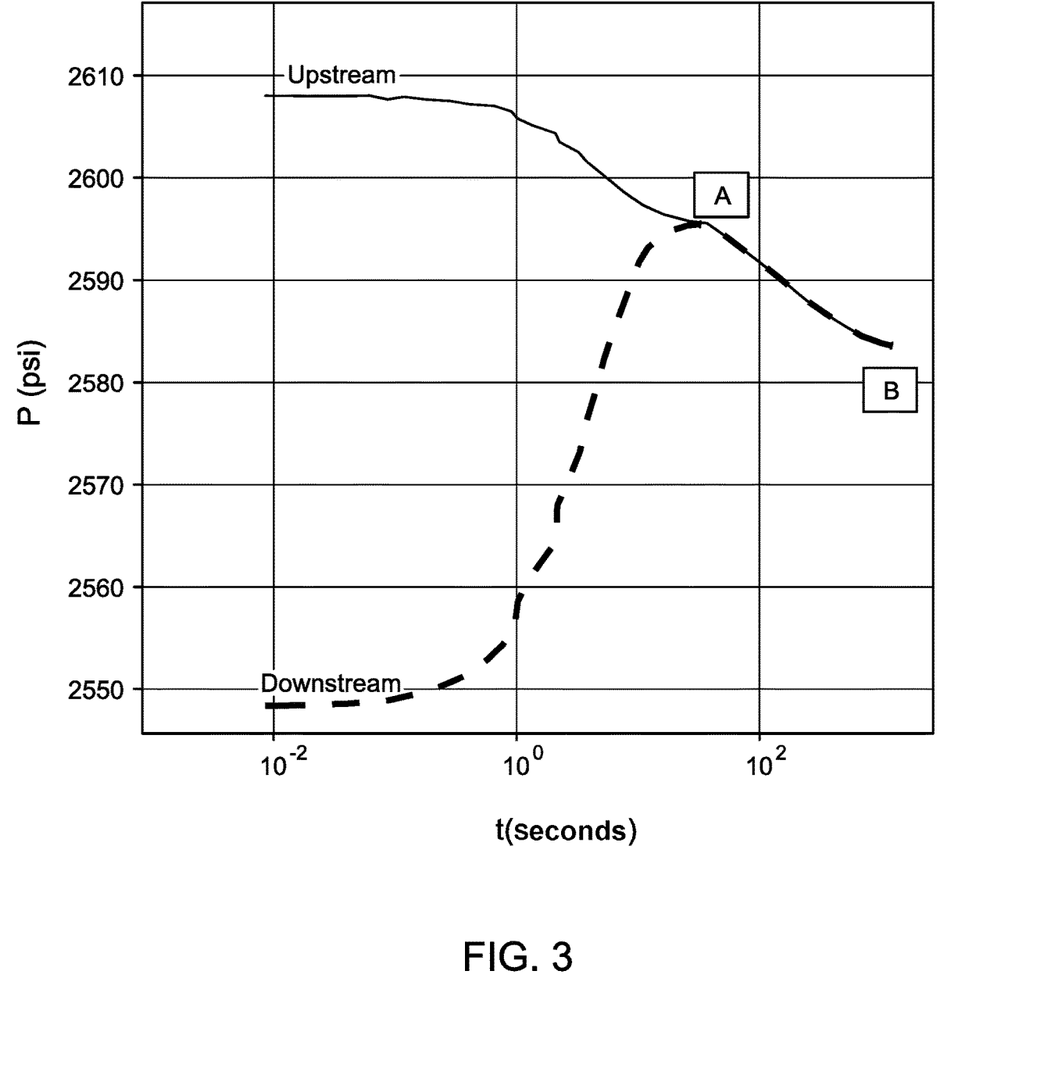
FIG. 3 is a graph illustrating upstream pressure and downstream pressure as a function of time in a pulse-decay experiment, according to one example embodiment of the disclosure.

FIG. 3 shows a typical plot for upstream and downstream pressures as a function of time from a pulse-decay experiment. When gas starts to flow from the upstream gas reservoir to the core sample, the pressure in the upstream gas reservoir declines. When gas flow reaches the downstream gas reservoir, pressure in the downstream gas reservoir starts to increase. At a certain time ($t_A$) corresponding to point A in FIG. 3, both gas reservoirs have the same pressure. At the corresponding time $t_A$ and earlier, gas flow in the mobile continuum is the dominant flow mechanism because the gas exchange between the two continua is a slow process. After $t_A$, the gas exchange between the two continua become relatively important because flow in the mobile continuum is close to the zero as a result of the lack of pressure gradient between the two gas reservoirs. Since gas pressure in the mobile continuum is greater, flow occurs from the mobile continuum to the immobile continuum. Thus, the pressure in FIG. 3 keeps declining with time to the right of point A. At Point B, pressure will not change with time anymore when both gas reservoirs, the upstream reservoir and the downstream reservoir, and both continua, the mobile continuum and immobile continuum, are in equilibrium.

Because at time $t_A$ both gas reservoirs and the mobile continuum have the same gas pressure, $P_A$, and the immobile continuum may still be at pressure, $P_{saturation}$, as a result of negligible gas exchange between the two continua, the following mass balance equation would apply:

$$(V_u + V_d + V_f)\rho_{saturation} + (V_u)\rho_{pulse} = (V_u + V_d + V_f)\rho_A \quad (3)$$

$$\phi_f = \frac{V_f}{V_{bulk}};$$

$$\phi_f < \phi_t$$

where $V_f$ is the pore volume of the mobile continuum, $\phi_f$ is the porosity purely from the mobile continuum, $\Phi_f = V_f/V_{bulk}$, and $\rho_{saturation}$, $\rho_{pulse}$, $\rho_A$ are gas densities corresponding to pressures of $P_{saturation}$, $P_{pulse}$, and $P_A$, respectively; $\phi_t$ is the total porosity including the porosity from both the mobile and immobile continua.

From Equation (3), the porosity $\phi_f$ is determined. The porosity from the mobile continuum, rather than total porosity $\phi_t$, is used to estimate permeability using Equation (2). It should be noted that Equation (3) can be applied to Point B in FIG. 3 and the form is shown in Equation (4). Because both gas reservoirs, mobile continuum and immobile continuum, are in equilibrium, the calculated $V_t$ from Equation (4) will be the total pore volume of the core sample. Thus the calculated $\phi_t$ becomes the total porosity.

$$(V_u + V_d + V_t)\rho_{saturation} + (V_u)\rho_{pulse} = (V_u + V_d + V_t)\rho_B \quad (4)$$

$$\phi_t = \frac{V_t}{V_{bulk}};$$

This method was applied to four rock samples used in pulse-decay experiments, as shown in Table 1. The $k_{new\ method}$ is estimated with the disclosed method and $k_{previous\ method}$ is the permeability estimated with total porosity. The relative difference in the table is defined as the ratio of the absolute difference between the two permeability values to $k_{new\ method}$ value. The relative difference is as large as 36%, indicating the importance to use an improved method to determine permeability.

EXPERIMENTAL DATA

Table 1 compares permeability values obtained using methods according to one or more example embodiments disclosed and prior methodologies.

|  | $k_{new\ method}$ (nD) | $k_{previous\ method}$ (nD) | Relative difference (%) |
| --- | --- | --- | --- |
| Test 1 | 8597 | 11144 | 30 |
| Test 2 | 6267 | 8300 | 32 |
| Test 3 | 3762 | 4981 | 36 |
| Test 4 | 2263 | 2598 | 15 |

Figure 4:
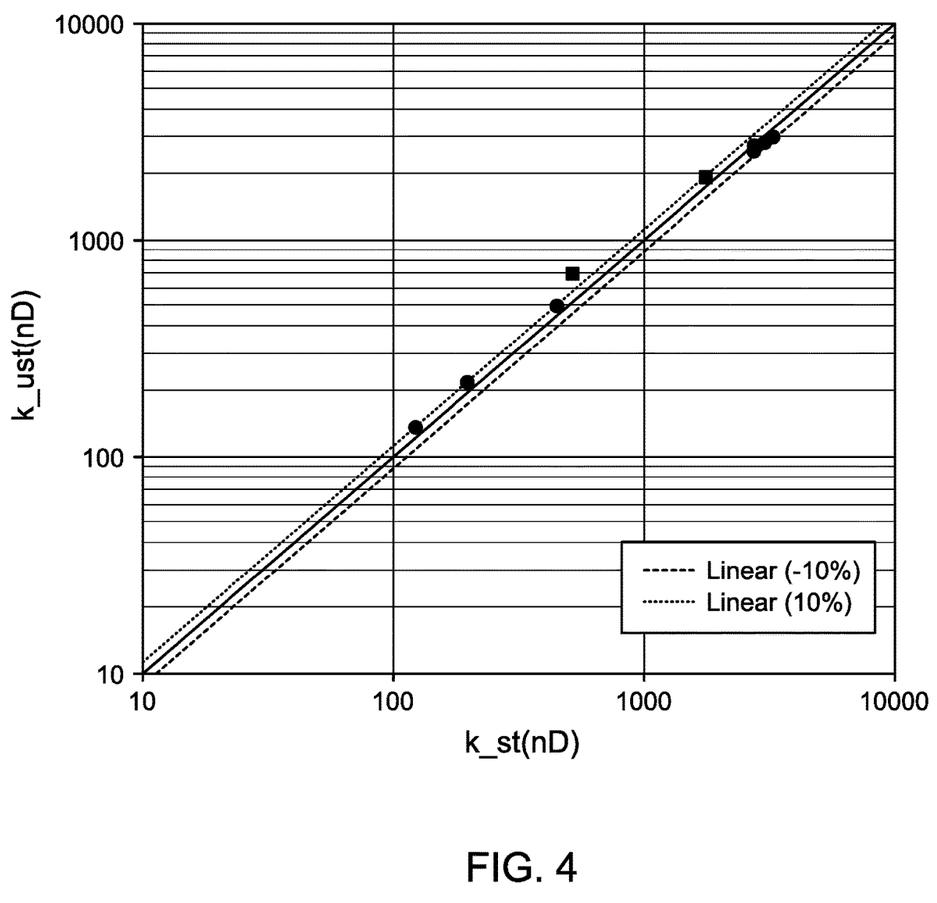
FIG. 4 is a graph comparing permeability values obtained from pulse-decay measurements according to one example embodiment of the disclosure with steady state permeability results for the same set of samples.

To validate the accuracy of the disclosed method, the estimated permeability values from the steady-state flow method are compared to those from the pulse-decay experiments based on the proposed method for the same rock samples, as shown in FIG. 4. Here, the values obtained from the disclosed method are plotted on the Y-axis (k_ust, in nano Darcies or nD), and the values from the steady-state flow method are plotted on the X-axis (k_st, in nD) of the graph. In the steady-state flow method, a steady-state flow is established for a core sample and then permeability is calculated with Darcy's law based on the observed fluid flux and pressure gradient along the core. Thus, permeability estimation in the steady-state flow method does not involve porosity. As indicated in FIG. 4, the permeability estimated with the disclosed method and that determined from the steady-state flow method for each core sample are very close and their relative difference is generally within a range of ±10%. This indicates the validity and reliability of the disclosed method.

Figure 5:
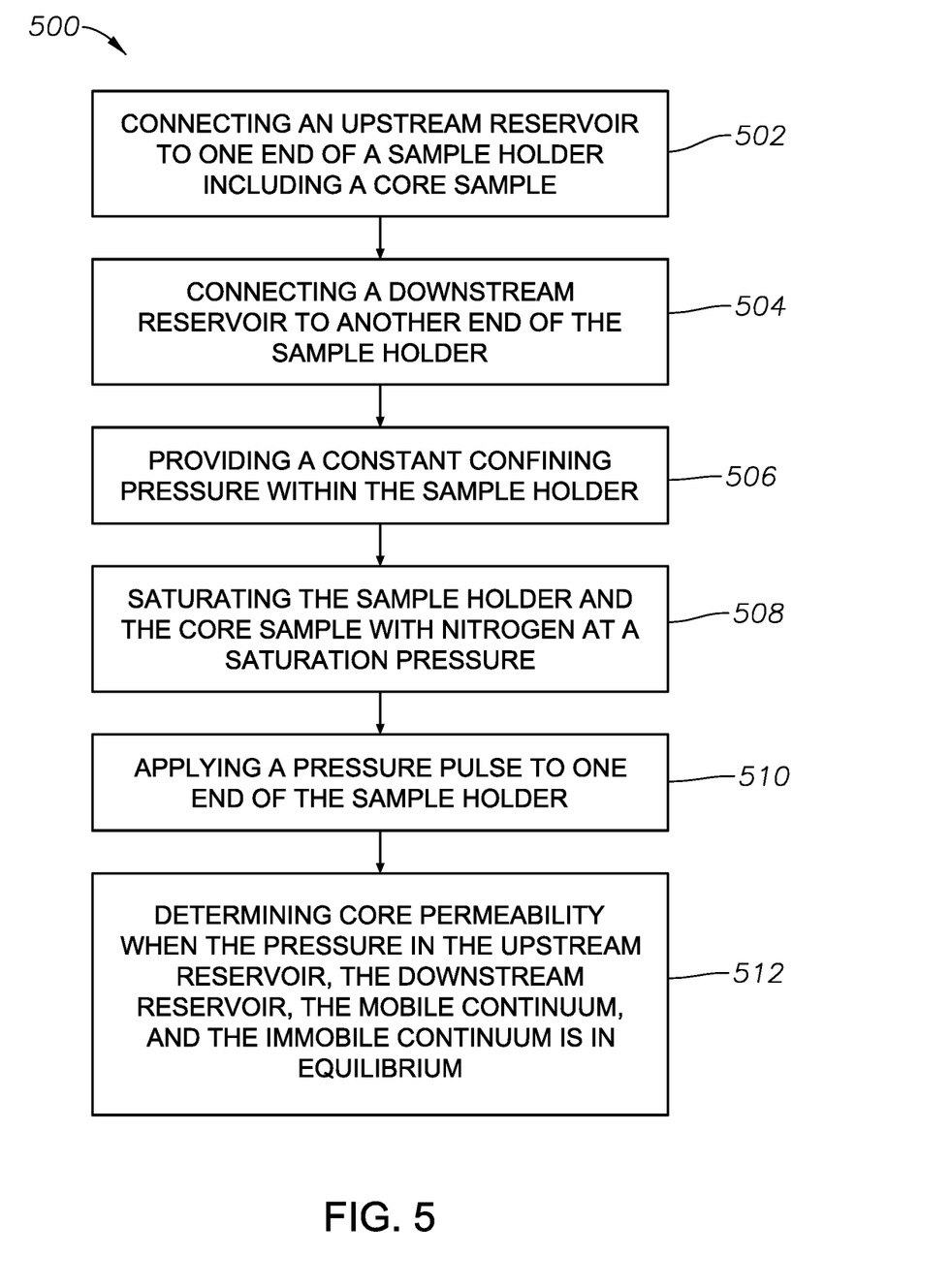
FIG. 5 shows a flow chart illustrating example operations in a method for determining core permeability of a subsurface formation, according to one example embodiment of the disclosure.

FIG. 5 shows a flow chart illustrating example operations in a method 500 for determining core permeability of a subsurface formation, according to one example embodiment of the disclosure. At step 502, the method 500 includes connecting an upstream reservoir to one end of a sample holder comprising a core sample of a subsurface formation. At step 504, the method includes connecting a downstream reservoir connected to another end of the sample holder. At step 506, the method includes providing a constant confining pressure ($P_A$) within the sample holder. At step 508, the method includes saturating the sample holder and the core sample with nitrogen at a saturation pressure, $P_{saturation}$. At step 510, the method includes applying a pressure pulse, $P_{pulse}$, to one end of the sample holder. At step 512, the method includes determining core permeability when the pressure in the upstream reservoir, the downstream reservoir, the mobile continuum, and the immobile continuum is in equilibrium. The step of determining core permeability of the subsurface formation may be performed using the formula:

$$P_u(t)-P_d(t)=f(\phi_f,L,A,V_{bulk},c,\mu,V_f,V_u,V_d,k,t)$$

where '$\Phi_f$' is the porosity of the sample from the mobile continuum, 'L' is the sample length, 'A' is the cross-sectional area of the sample, '$V_{bulk}$' is the bulk volume of the sample (where $V_{bulk}$=LA; and $\phi=V_s/V_{bulk}$), 'c' is the gas compressibility, '$\mu$' is the gas viscosity, '$V_f$' is the pore volume of the mobile volume, '$V_u$' is the upstream reservoir volume, '$V_d$' is the downstream reservoir volume, '$P_u(t)$' is the pressure of the upstream side, '$P_d(t)$' is the pressure of the downstream side, 'k' is the sample permeability, and 't' is time.

Figure 6:
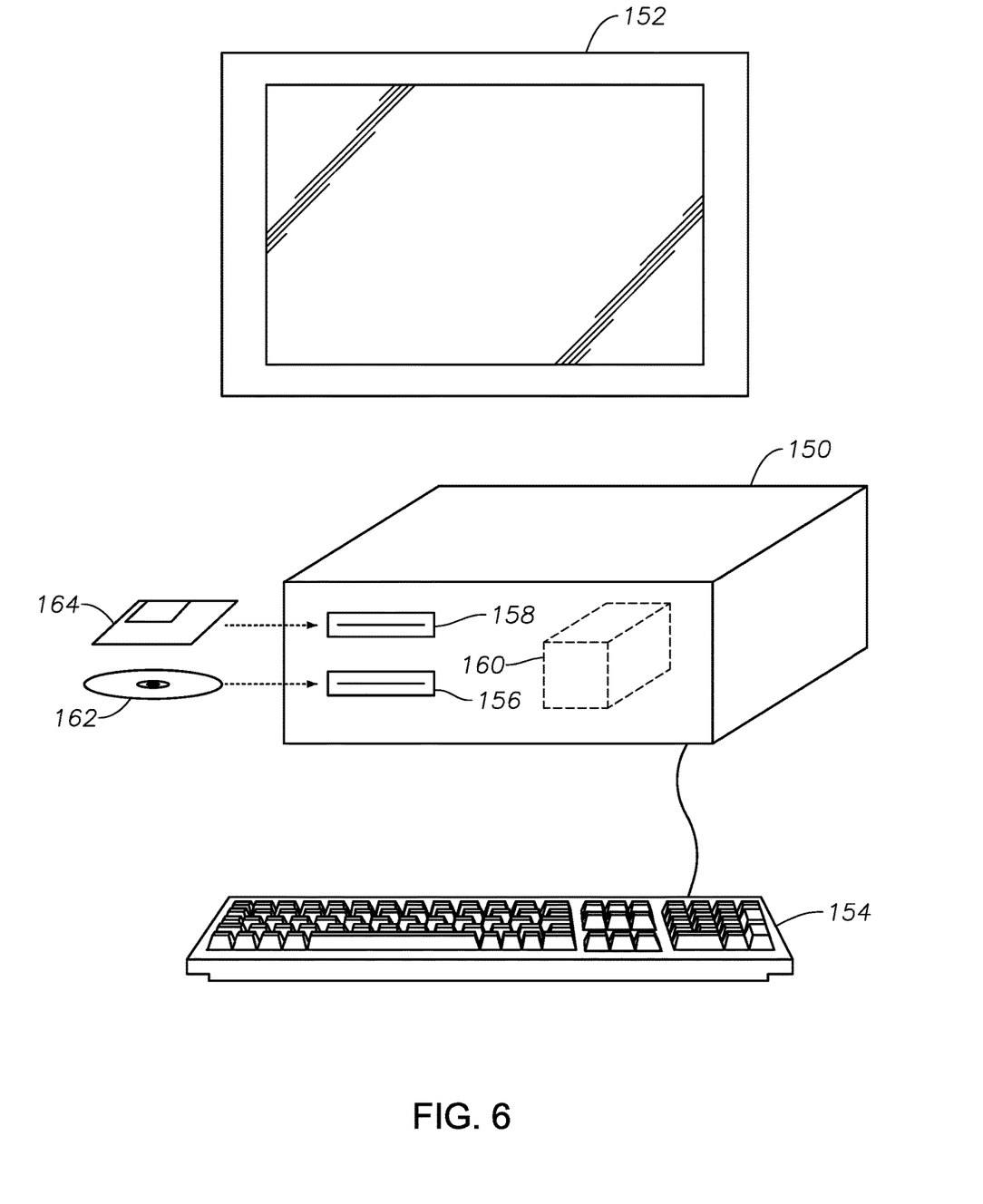
FIG. 6 illustrates a special purpose computer system for determining core permeability of a subsurface formation, according to one example embodiment of the disclosure.

Another example embodiment is a special purpose computer configured to execute specific computer instructions in a computer program stored in computer readable media. Referring to FIG. 6, the foregoing process as explained with reference to FIGS. 1-5 can be embodied in computer-readable code. The code can be stored on, for example, a computer readable medium, such as a floppy disk 164 which may be read by a disk drive 158, CD-ROM 162 which may be read by a disk drive 156, or a magnetic (or other type) hard drive 160 forming part of a general purpose programmable computer. The computer, as known in the art, includes a central processing unit 150, a user input device such as a keyboard 154 and a user display 152 such as a flat panel LCD display or cathode ray tube display. According to this aspect, the computer readable medium includes logic operable to cause the computer to execute acts as set forth previously and explained with respect to the previous figures.

Although the technology has been described with reference to particular embodiments, it is to be understood that these embodiments are merely illustrative of the principles and applications of the present technology. It is therefore to be understood that numerous modifications may be made to the illustrative embodiments and that other arrangements may be devised without departing from the spirit and scope of the present technology as defined by the appended claims.

The invention claimed is:

1. A method for determining core permeability in pulse decay experiments, the method comprising the steps of:
    connecting an upstream reservoir to one end of a sample holder holding a core sample of a subsurface formation;
    connecting a downstream reservoir to another end of the sample holder;
    providing a constant confining pressure ($P_c$) within the sample holder;
    saturating the sample holder and the core sample with nitrogen at a saturation pressure, $P_{saturation}$;
    applying a pressure pulse, $P_{pulse}$, to one end of the sample holder; and
determining core permeability when a pressure in the upstream reservoir, the downstream reservoir, and a mobile continuum within the core sample, is in equilibrium wherein the core permeability is determined using the formula:

$$P_u(t)-P_d(t)=f(\phi_f,L,A,V_{bulk},c,\mu,V_f,V_u,V_d,k,t)$$

where '$\Phi_f$' is the porosity of the sample from the mobile continuum, 'L' is the sample length, 'A' is the cross-sectional area of the sample, '$V_{bulk}$' is the bulk volume of the sample (where $V_{bulk}$=L A; and $\Phi_f=V_f/V_{bulk}$), 'c' is the gas compressibility, '$\mu$' is the gas viscosity, '$V_f$' is the pore volume of the mobile continuum, '$V_u$' is the upstream reservoir volume, '$V_d$' is the downstream reservoir volume, '$P_u(t)$' is the pressure of the upstream side, '$P_d(t)$' is the pressure of the downstream side, 'k' is the sample permeability, and 't' is time.

2. The method according to claim 1, wherein the porosity of the sample from the mobile continuum is determined using the formula:

$$(V_u+V_d+V_f)\rho_{saturation}+(V_u)\rho_{pulse}=(V_u+V_d+V_f)\rho_A$$

$$\phi_f=\frac{V_f}{V_{bulk}};$$

where $V_f$ is the pore volume of the mobile continuum, and $\rho_{saturation}$, $\rho_{pulse}$, $\rho_A$ are gas densities corresponding to pressures of $P_{saturation}$, $P_{pulse}$, and $P_A$, respectively, and subscript A indicates the time when the pressure inside the upstream reservoir, the downstream reservoir, and the mobile continuum reaches equilibrium.

3. The method according to claim 2, wherein $$f(\phi_f,L,A,V_{bulk},c,\mu,V_s,V_u,V_d,k,t)\propto\frac{kt}{c\mu\phi_f L^2}$$

at a certain time.

4. The method according to claim 1, wherein when the pressure pulse is applied to one end of the sample holder, gas flows from a mobile continuum to an immobile continuum because the gas pressure is higher in the mobile continuum than the immobile continuum.

5. The method according to claim 1, wherein the confining pressure is in the range of about 3,000 psi to 10,000 psi.

6. The method according to claim 1, wherein the saturation pressure is about 2,500 psi or more.

7. The method according to claim 1, wherein a pressure applied by the pressure pulse is about 100 psi or more.

8. A system for determining core permeability, the system comprising:
    a sample holder holding a core sample of a subsurface formation;
    an upstream reservoir connected to one end of the sample holder;
    a downstream reservoir connected to another end of the sample holder;
    an inlet pump connected to the upstream reservoir;
    an outlet pump connected to the downstream reservoir;
    a plurality of pressure sensors connected to the upstream reservoir, the downstream reservoir, and the sample holder; and
    a processor configured to receive signals from the plurality of pressure sensors, and determine the core permeability based on a pressure in the upstream reservoir and a pressure in the downstream reservoir, wherein the system is further configured to:
        provide a constant confining pressure ($P_c$) within the sample holder;
        saturate the sample holder and the core sample with nitrogen at a saturation pressure, $P_{saturation}$; and apply a pressure pulse, $P_{pulse}$, to one end of the sample holder, wherein the core permeability is determined using the formula:

$$P_u(t)-P_d(t)=f(\phi_f,L,A,V_{bulk},c,\mu,V_f,V_u,V_d,k,t)$$

where '$\Phi_f$' is the porosity of the sample from the mobile continuum, 'L' is the sample length, 'A' is the cross-sectional area of the sample, '$V_{bulk}$' is the bulk volume of the sample (where $V_{bulk}$=L×A; and $\phi=V_s/V_{bulk}$), 'c' is the gas compressibility, '$\mu$' is the gas viscosity, '$V_f$' is the pore volume of the mobile continuum, '$V_u$' is the upstream reservoir volume, '$V_d$' is the downstream reservoir volume, '$P_u(t)$' is the pressure of the upstream side, '$P_d(t)$' is the pressure of the downstream side, 'k' is the sample permeability, and 't' is time.

9. The system according to claim 8, wherein the core sample comprises a mobile continuum and an immobile continuum.

10. The system according to claim 8, wherein the pressure in the upstream reservoir is equal to the pressure in the downstream reservoir.

11. The system according to claim 8, wherein the step of determining core permeability is performed when the pressure in the upstream reservoir, the downstream reservoir, the mobile continuum, and the immobile continuum is in equilibrium.

12. The system according to claim 8, wherein the porosity of the mobile continuum is determined using the formula:

$$(V_u + V_d + V_f)\rho_{saturation} + (V_u)\rho_{pulse} = (V_u + V_d + V_f)\rho_A$$

$$\phi_f = \frac{V_f}{V_{bulk}};$$

where $V_f$ is the pore volume of the mobile continuum, and $\rho_{saturation}$, $\rho_{pulse}$, $\rho_A$ are gas densities corresponding to pressures of $P_{saturation}$, $P_{pulse}$, and $P_A$, respectively, '$\Phi_f$' is the porosity of the sample from the mobile continuum.

13. The system according to claim 8, wherein the confining pressure is in the range of about 3,000 psi to 10,000 psi.

14. The system according to claim 8, wherein the saturation pressure is about 2,500 psi or more.

15. The system according to claim 8, wherein the pressure applied by a pressure pulse is about 100 psi or more.

16. A computer program for use in a method for determining core permeability, the method comprising the steps of:
connecting an upstream reservoir to one end of a sample holder holding a core sample of a subsurface formation;
connecting a downstream reservoir to another end of the sample holder;
providing a constant confining pressure ($P_c$) within the sample holder;
saturating the sample holder and the core sample with nitrogen at a saturation pressure, $P_{saturation}$;
applying a pressure pulse, $P_{pulse}$, to one end of the sample holder; and
the computer program comprising program instructions that when executed by a processor, cause the processor to determine core permeability of the subsurface formation using the formula:

$$P_u(t)-P_d(t)=f(\phi_f,L,A,V_{bulk},c,\mu,V_f,V_u,V_d,k,t)$$

where '$\Phi_f$' is the porosity of the sample from the mobile continuum, 'L' is the sample length, 'A' is the cross-sectional area of the sample, 'Vbulk' is the bulk volume of the sample (where Vbulk=L A; and $$\Phi_f = \frac{V_f}{V_{bulk}}\Big),$$

'c' is the gas compressibility, '$\mu$' is the gas viscosity, '$V_f$' is the pore volume of the mobile continuum, 'Vu' is the upstream reservoir volume, '$V_d$' is the downstream reservoir volume, 'Pu(t)' is a pressure of the upstream side, 'Pd(t)' is a pressure of the downstream side, 'k' is the sample permeability, and 't' is time.

* * * * *